United States Patent [19]

Tiede et al.

[11] Patent Number: 5,172,703
[45] Date of Patent: Dec. 22, 1992

[54] TORSION CONTROL HARNESS

[76] Inventors: Michelle Tiede, 840 Rice St. N., Kasota, Minn. 56050; Schelli McCabe, Rte. 1, Box 448, Madison Lake, Minn. 56063

[21] Appl. No.: 780,994

[22] Filed: Oct. 23, 1991

[51] Int. Cl.$^5$ ............................................. A61F 3/00
[52] U.S. Cl. .................... 128/875; 128/869; 128/876; 602/23
[58] Field of Search .................. 128/68, 80 R, 80 A, 128/80 B, 80 E, 846, 845, 869, 874, 875, 876, 68-80 E; 602/23, 24, 25, 27, 28, 29

[56] References Cited

U.S. PATENT DOCUMENTS

| 806,403 | 12/1905 | DuPell | 128/80 R |
|---|---|---|---|
| 1,930,378 | 10/1933 | Beagan | 128/875 X |
| 2,062,586 | 12/1936 | Lawrence | 128/875 |
| 4,484,572 | 11/1984 | Dobson | 128/875 |
| 4,901,710 | 2/1990 | Meyer | 128/80 A X |
| 4,913,136 | 4/1990 | Chong et al. | 128/80 R X |
| 5,027,833 | 7/1991 | Calkin | 128/846 X |
| 5,040,524 | 8/1991 | Votel et al. | 128/845 X |

FOREIGN PATENT DOCUMENTS

| 770488 | 10/1980 | U.S.S.R. | 128/80 R |
|---|---|---|---|
| 2206494 | 1/1989 | United Kingdom | 128/68 |

Primary Examiner—Robert A. Hafer
Assistant Examiner—Sam Rimell
Attorney, Agent, or Firm—Douglas L. Tschida

[57] ABSTRACT

A soft-tissue correctional aide supported at the hips and shoulders and including a plurality of resilient straps which mount to shoes or other anchoring appliances containing mating fasteners. The straps are trainable about the hips and legs to the anchor fasteners to provide a relatively constant correctional bias, yet permit normal body movement. A length adjustable belt anchors the assembly to the waist and a pair of length adjustable suspenders anchor the belt to the shoulders. The straps mount directly to the belt or to one or more sleeves supported along the belt.

8 Claims, 5 Drawing Sheets 5,172,703

TORSION CONTROL HARNESS

BACKGROUND OF THE INVENTION

The present invention relates to exo-skeleton or soft-tissue supports and, in particular, to an under or over garment harness or "dynamic splint" for correcting walking posture.

Fillauer bars, Denis-Browne bars, Brackman skates, counter splints and Ganley splints have all been used to correct various types of rotational or positional deformities. McCrea, J. D., of Pediatric Orthopedics of the Lower Extremity pp. 330-332. (Futura Publishing Co, 1985) Each of these devices generally includes a rigid bar or extension and means for securing the bar between the feet of a user to correct a soft tissue deformity. The splints are normally worn during sleep which can produce inconvenience to the patient and those attending the patient and especially when used with minor children.

A "twister cable" assembly is also disclosed which binds individual cables at the knees with a separate attachment at the shoes. Cable tension is adjusted at the leg attachment straps.

Due to the inherent rigidity of the bars and cables of the above present in appliances, these devices have not been found to be particularly conducive to use with children. The activity levels of children demands a more elastic restraint to accommodate dynamic activity, both during sleep and while awake.

SUMMARY OF THE INVENTION

It is accordingly a primary object of the present invention to provide a dynamic exo-skeleton or soft-tissue brace or splint means for providing a therapeutic bias to a preferred body part, with minimal interference to normal activity and use of the affected limb.

It is a further object of the invention to provide a brace which anchors to a trunk portion of the body and provides a resilient and directionally sustainable pressure to various portions of the body whereat an opposite end of the restraint is secured.

It is a further object of the invention to anchor the brace to the hips and shoulders.

It is a further object of the invention to provide a brace including a plurality of length adjustable, elastic members which can be selectively trained about the body trunk to mount to anchor means provided at selected other body parts.

It is a still further object of the invention to provide an assembly which provides a wide range of adjustment and fitting to users of different sizes and shapes.

It is a still further object of the invention to provide a launderable assembly.

Various of the foregoing objects and advantages are particularly obtained in one presently preferred construction which includes a belt and to which are appended a suspenders assembly and a plurality of elastic torsion control straps. The belt comprises a wide-width web member and contains Velcro fasteners. Strap ends of the suspenders assembly extend from the belt and mate with one another at length adjustment fasteners. The relative mounting of the belt and suspenders can be adjusted to fit a variety of body shapes and sizes.

Secured directly to the belt or to sleeves adjustably mounted along the belt are a plurality of length adjustable, elastic torsion control straps. Each strap includes length adjustment means and fastener means for securing the straps to an anchor means separately secured to a body part whereat correctional adjustment is desired. In the preferred embodiment, the fasteners mount to inner and outer, fastener containing surfaces of a pair of shoes. The straps, in turn, may be wrapped about the hips and legs to provide internally or externally directed torsion control.

Still other objects, advantages and distinctions of the invention will become more apparent upon reference to the following detailed description with respect to the appended drawings. The description is intended to be illustrative only of presently considered constructions and various improvements and modifications thereto. The description should not be strictly construed, but rather should be interpreted within the scope of the following appended claims.

DESCRIPTION OF THE PREFERRED EMBODIMENTS

Figure 1:
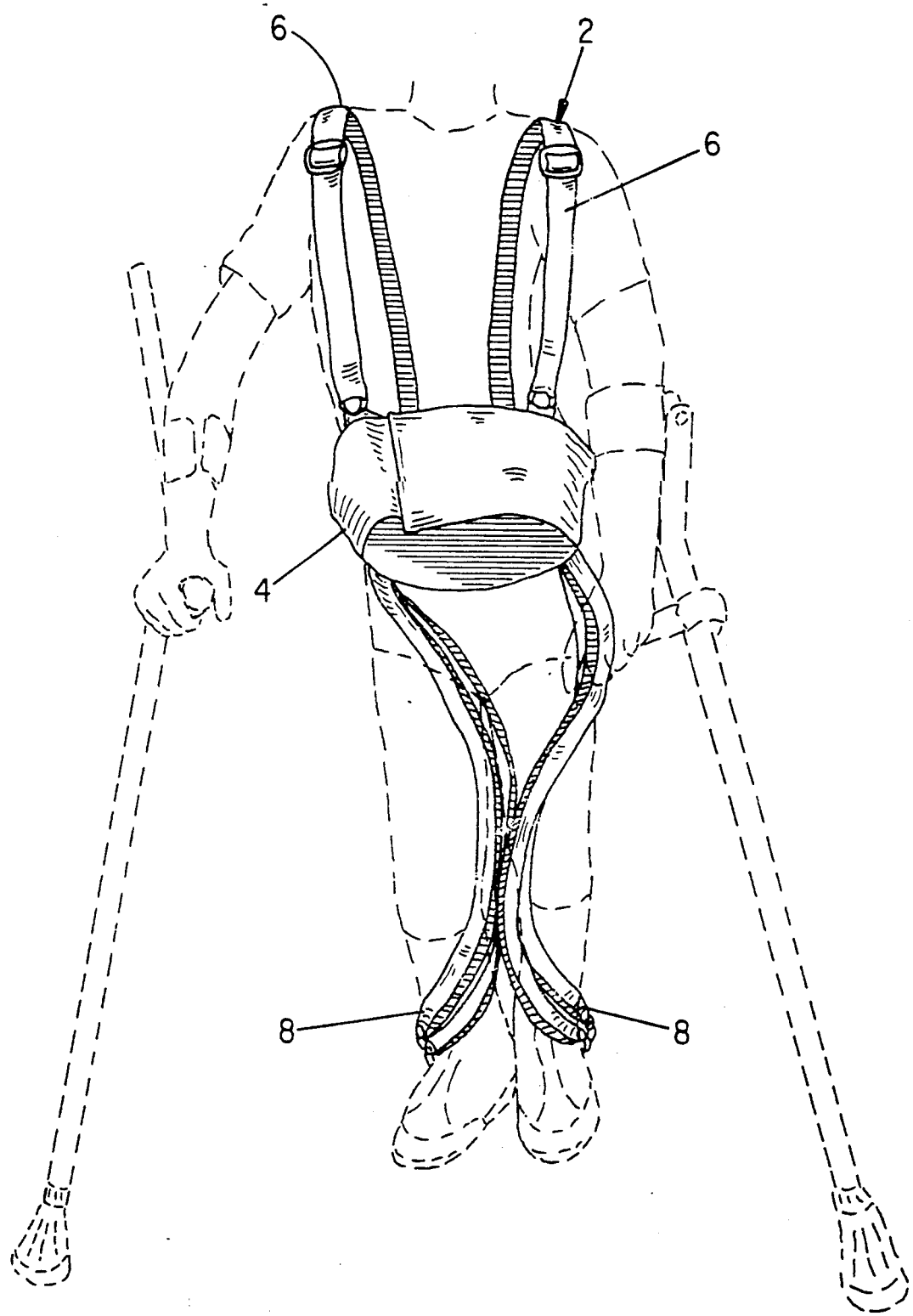
FIG. 1 is a perspective drawing of the invention mounted to provide external torsion control and fitted as an undergarment to a user (shown in phantom).
Figure 2:
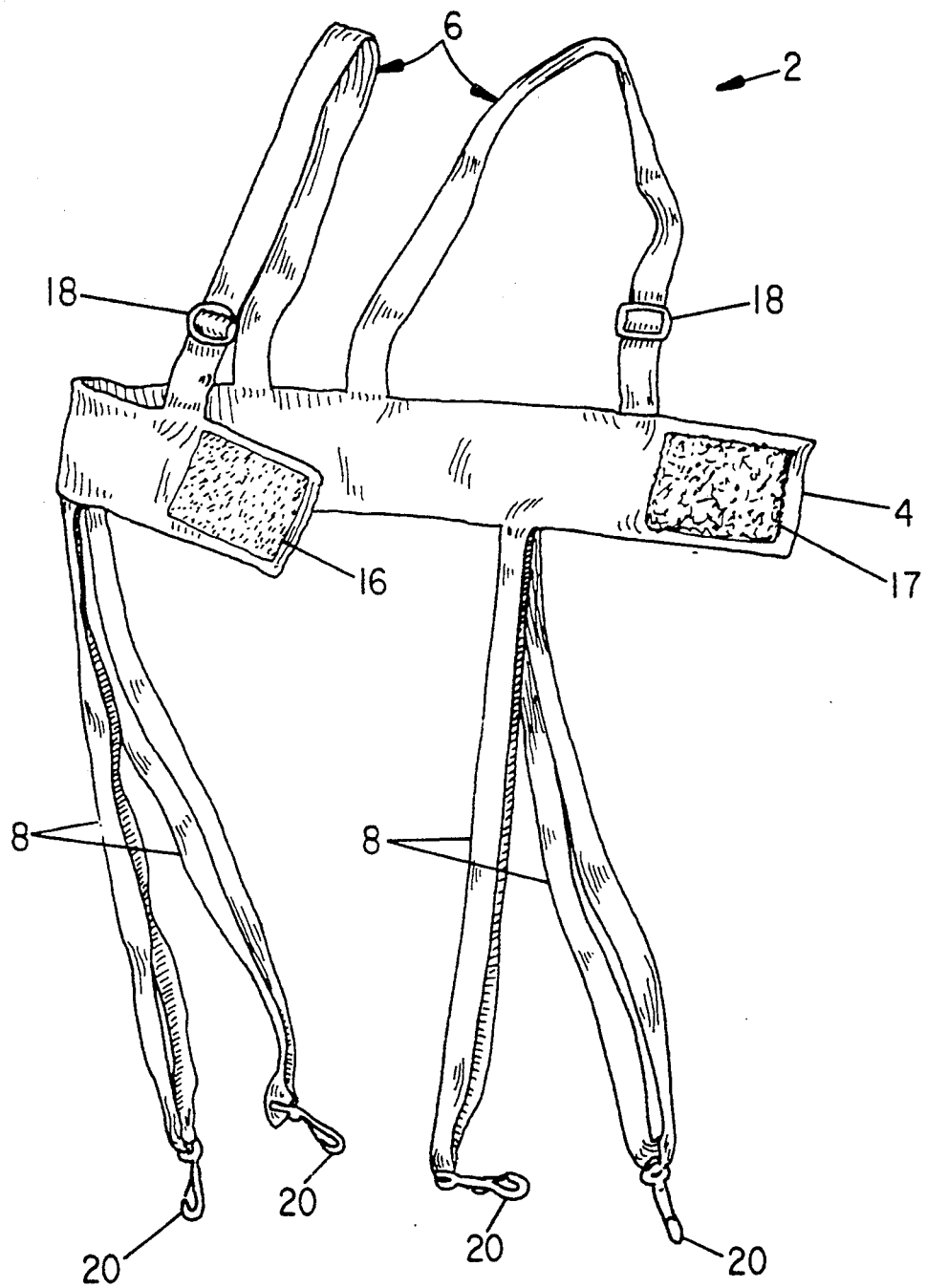
FIG. 2 is a detailed perspective drawing of the assembly of FIG. 1.

Referring to FIG. 1, a perspective drawing is shown of an under-garment assembly 2 as it appears when normally fit to a typical user (shown in phantom). FIG. 2 further depicts the assembly 2, when removed from the user.

Generally, the assembly 2 provides a length adjustable belt 4 and to which is secured a pair of length adjustable suspenders assembly 6 and a plurality of tensioning strap assemblies 8. In normal use, the belt 4 is fit to the waist of the user and the suspenders 6 are secured about the user's shoulders. Appropriate length adjustments are made to properly fit the belt 4 to the waist and the suspenders 6 to the shoulders.

Figure 3:
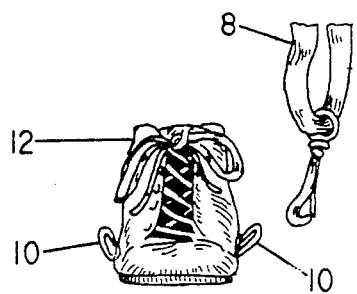
FIG. 3 depicts an end of a strap in relation to a shoe containing fasteners on the inner and outer shoe surfaces.
Figure 4:
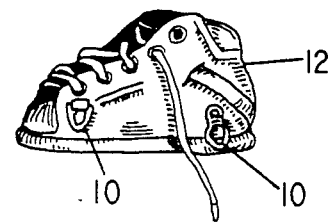
FIG. 4 is an elevation drawing of a typical shoe which receives the strap fasteners.

Extending from the belt 4 are individual tension control straps 8. The straps 8 can be affixed at a single or multiple locations along the belt 4 and may either be permanently or removably mounted to the belt 4. For the arrangement shown, the straps 8 extend from the belt 4 and behind the waist and hips of the user to wrap over the forward surfaces of the shins and clip to outside fasteners mounted to a pair of shoes 12 (reference FIGS. 3 and 4). A corresponding external, torsional pressure is thus applied about the legs of the user to induce the feet to point inward and correct for an out-toeing condition. Alternatively, the straps 8 can be trained about the front surfaces of the thighs and attach to inside fasteners 10 provided at each shoe. An internal torsional adjustment is thereby provided to correct for an in-toeing condition. Numerous other strap mountings can be effected as necessary to correct for other soft tissue misalignment. Depending upon the condition, the straps 8 may be secured to different locations of the shoe. The details of the particular mounting will become more apparent below.

The specific torsional tension is determined from the relative length established for each strap 8 and the elasticity of each strap. Provided the user maintains an erect posture, a substantially constant force induces an opposite, sustained corrective force to realign the related body part to which the ends of the straps 8 are secured. The elasticity of the straps 8 not only accommodate the required torsional correction but also normal body movements of the affected limbs, such as during walking. The assembly 2 may also be worn during sleep.

Figure 5:
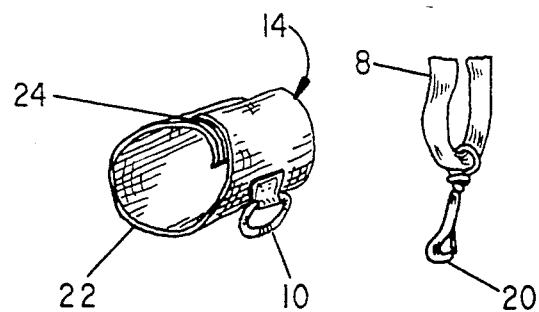
FIG. 5 is a perspective drawing of a fastener containing anchor cuff which can be mounted to selected limbs of the exo-skeleton.

Although the assembly 2 is configured to mount to a pair of shoes 12, other anchoring appliances, such as a cuff assembly 14 of FIG. 5, can be fitted to other limb parts to receive the straps 8. For example, with the mounting of one or more cuffs 14, the straps 8 might be secured to the wrists, elbows, knees, shoulders or still other body parts which are maladjusted. Related fasteners 10 appended to the cuff 14 receive the straps 8, when properly trained about the body trunk to appropriately direct the corrective forces.

While the suspenders 6 further stabilize the anchoring of the assembly 2 to the body, on occasion, they can be deleted and the belt 4 used alone. Preferably, multiple anchor points stabilize and distribute the counter-forces of the straps 8 at the reference end over a large body area. The active end of the straps 8 otherwise are secured in specific relation to the body part being corrected. User comfort and the "wear time" of the assembly 2 is thereby increased.

With attention to FIG. 2, the belt 4 particularly comprises a length of a durable and/or corded material, such as heavy canvas, having a web width in the range of two to four inches. The cut ends or edges of the material are hemmed to prevent fraying. Provided along inner and outer mating surfaces of the belt 4 are pieces 16 and 17 of mating hook and loop Velcro fastener material and whereby the length of the belt 4 can be adjusted, depending upon the amount of overlap.

Permanently hemmed along the upper periphery of the belt 4 are the suspenders 6. Secured along each suspender 6 are looped adjusters 18, whereby the suspender length may be tailored to the body trunk. Alternatively, the suspenders 8 may either be deleted from the belt 4 or detachably secured thereto in the fashion of the assembly 34 of FIG. 6.

Anchored at common hem points along the sides of the lower edges of the belt 4 are pairs of tension control straps 8. The mounting position of the straps may be varied as desired relative to the condition to be treated. The straps 8 may also all be hemmed to a common location, such as the center of the belt 4. The straps 8 can also include length adjusters 18 (reference FIGS. 5 and 6) or not (reference FIGS. 1 and 2).

If not included and depending upon the mounting location of the straps 8, the strap length is controlled by varying the number of wraps and the location of the wraps along the body trunk. Secured to the outer ends of each strap 8 are safety clip fasteners 20 which mate with the D-fasteners 10 appended to the shoes 12. Other types of fasteners 20 may be secured to the shoes 12 and straps 8.

In lieu of mounting the straps 8 to shoes 12 (reference FIGS. 3 and 4), FIG. 5 depicts an anchor cuff 14. Like the belt 4, the cuff 14 is length adjustable and can be secured to selected limbs or portions of the exo-skeleton, such as the wrists, elbows, ankles, or knees. Each cuff 14 provides a web of material, such as leather or fabric of two to six inches in width and whereto fasteners 10 are secured which retain the straps 8. Mating Velcro fasteners 24 sewn to the body of the cuff 22 permit length adjustment.

An example of one use of the cuff 14 might encompass a circumstance where torsional adjustment is required to the arms. For this circumstance, the belt 4 can be raised to mount beneath the arm pits and wherefrom the straps 8 can be appropriately trained about the arms to mount to anchor cuffs 14 secured along the arms.

Figure 6:
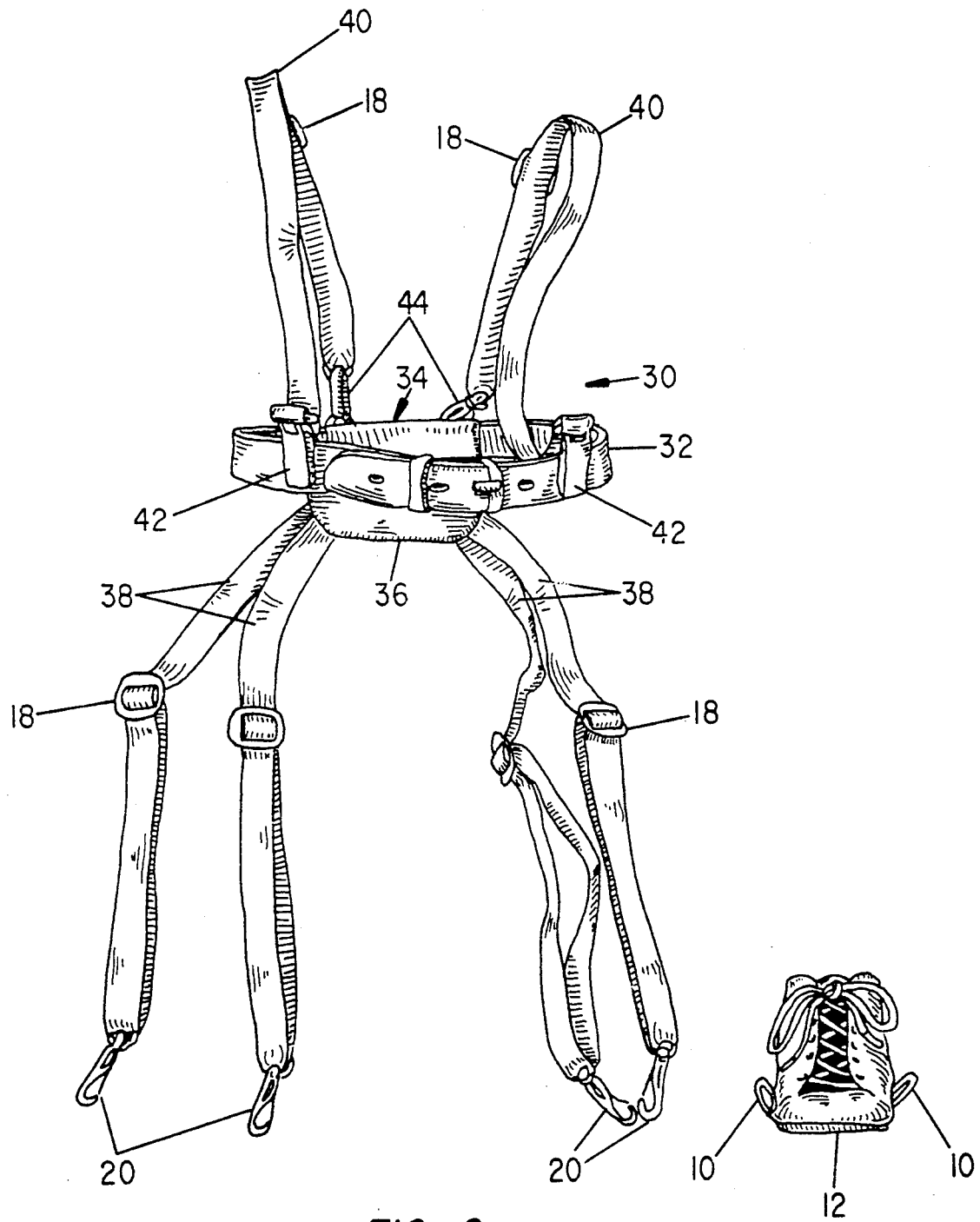
FIG. 6 is a perspective drawing of an alternative over-garment construction of the invention, wherein the tensioning straps are mounted to a sleeve affixed to a belt.
Figure 7:
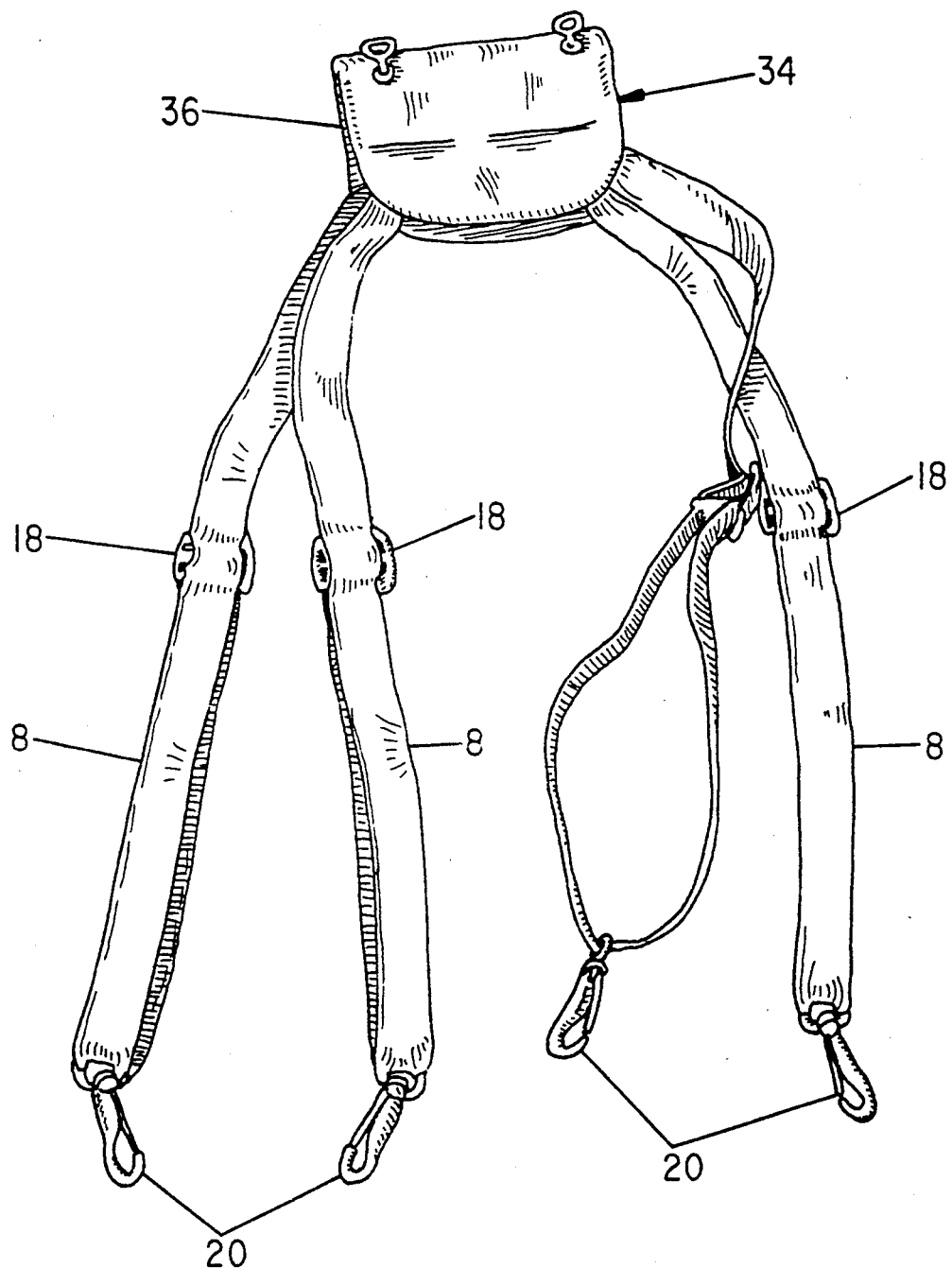
FIG. 7 is a detailed perspective drawing of the sleeve assembly of FIG. 6.

With attention lastly directed to FIGS. 6 and 7, an over-garment assembly 30 is depicted. This assembly uses a conventional leather belt 32 and whereto one or more torsion sleeve assemblies 34 are slideably mounted. The sleeve assembly 34 is constructed of a length of leather which is hemmed to a tubular sleeve 36 that is sized to mount over the belt 32. Also hemmed to the sleeve 36 are individual length adjustable tension straps 38. Each strap 38 is looped in relation to an active end mounted clip fastener 20 and an intermediate length adjuster 18. Each strap 38 can be separately length adjusted to the individual to appropriately direct correctional forces when wrapped about the body trunk.

Removably secured otherwise to the belt 4 are individual suspenders 40. Each suspender 40 can be separately length adjusted via an adjuster 18. Hinged clips 42 secure the front of the suspenders to the belt and loops 44 secure the back of each suspender to the belt 32.

While the invention has been described with respect to various presently considered constructions, improvements and modifications thereto, it is to be appreciated that still other configurations might suggest themselves to those skilled in the art. Accordingly, it is contemplated that the following appended claims should be interpreted to include all those equivalent embodiments within the spirit and scope thereof.

What is claimed is:

1. A soft tissue splint comprising:
 (a) strap means including a webbed portion for adjustably mounting about the waist and including suspender means having at least one support portion which is trainable about the shoulders for supporting said strap means from the shoulders;
 (b) a plurality of elastic members coupled at one end to said strap means; and
 (c) anchor means for mounting to the exo-skeleton comprising a pair of shoes wherein each shoe includes a plurality of fasteners for receiving mating fasteners secured to each of said elastic members upon training said elastic members about the exo-skeleton, whereby a rehabilitative correctional force may be applied to the exo-skeleton.

2. Apparatus as set forth in claim 1 wherein said strap means comprises an elastic web which mounts about the waist and which includes hook and loop fastener means secured to the opposite ends of said web for adjusting the length thereof.

3. Apparatus as set forth in claim 2 wherein the support portion is length adjustable.

4. Apparatus as set forth in claim 1 wherein each of said elastic members includes means for adjusting the length thereof relative to said shoes.

5. Apparatus as set forth in claim 1 wherein said plurality of elastic members are secured to a tubular means which selectively mounts along said strap means.

6. A soft tissue splint comprising:
 (a) strap means including an elastic webbed portion for adjustably mounting about the waist and including suspender means having at least one support portion which is trainable about the shoulders for supporting said strap means from the shoulders and which support portion is adjustable in length;
 (b) a plurality of elastic members coupled to said strap means and wherein each of said elastic members includes means for adjusting the length thereof; and
 (c) anchor means for mounting to the exo-skeleton comprising a pair of shoes and wherein each shoe includes a plurality of loop members for receiving mating fasteners secured to each of said elastic members upon training said elastic members about the exo-skeleton, whereby a rehabilitative correctional force may be applied to the exo-skeleton.

7. A soft tissue splint comprising;
 (a) waist strap means including a webbed portion for adjustably mounting about the waist and including suspender means having at least one support portion which is trainable about the shoulders for supporting the waist strap means from the shoulders;
 (b) a plurality of elastic members coupled at one end to said waist strap means; and
 (c) anchor strap means for mounting to the exo-skeleton at a point displaced from the waist strap means and including a plurality of fasteners for receiving mating fasteners secured to each of said elastic members upon training said elastic members about the exo-skeleton, whereby a rehabilitative correctional force may be applied to the exo-skeleton.

8. Apparatus as set forth in claim 7 wherein said anchor strap means comprises a pair of web members, wherein each web member includes means for adjusting the length of said web member and at least one loop member for receiving a mating fastener of one of said elastic members.

* * * * *